United States Patent [19]

Dao et al.

[11] Patent Number: 5,719,103
[45] Date of Patent: Feb. 17, 1998

[54] POWDER FORMULATION USEFUL FOR SEED TREATMENT AND FOLIAR TREATMENT OF PLANTS

[75] Inventors: Dong Cong Dao, Guelph; Heather Leigh Kelly, Stoney Creek, both of Canada

[73] Assignees: Uniroyal Chemical Company, Inc., Middlebury, Conn.; Uniroyal Chemical Ltd./Ltee, Elmira, Canada

[21] Appl. No.: 642,832

[22] Filed: May 2, 1996

[51] Int. Cl.$^6$ .......................... A01N 25/14; A01N 25/24
[52] U.S. Cl. .......................... 504/116; 424/407; 514/452
[58] Field of Search .......................... 504/116; 424/407; 514/952

[56] References Cited

U.S. PATENT DOCUMENTS

| | | | |
|---|---|---|---|
| 4,182,716 | 1/1980 | Znotins et al. | 549/14 |
| 4,319,033 | 3/1982 | Tsai et al. | 549/15 |
| 4,497,646 | 2/1985 | Rubio | 71/3 |
| 4,569,690 | 2/1986 | Brouwer et al. | 71/90 |
| 4,839,349 | 6/1989 | Covey et al. | 514/92 |
| 4,857,649 | 8/1989 | Lai et al. | 548/262 |
| 4,927,451 | 5/1990 | Brouwer et al. | 71/92 |
| 4,943,309 | 7/1990 | Bell | 71/74 |
| 4,943,678 | 7/1990 | Angyan et al. | 514/374 |
| 4,945,113 | 7/1990 | Nowakowski et al. | 514/605 |
| 4,950,671 | 8/1990 | Lai et al. | 514/277 |
| 4,966,910 | 10/1990 | Lai et al. | 514/383 |
| 4,966,912 | 10/1990 | Reylea et al. | 514/397 |
| 4,979,982 | 12/1990 | Brouwer et al. | 71/92 |
| 4,981,508 | 1/1991 | Strunk et al. | 71/92 |
| 5,010,068 | 4/1991 | Dekeyser et al. | 514/79 |
| 5,039,332 | 8/1991 | Friedlander et al. | 71/92 |
| 5,061,716 | 10/1991 | Reylea et al. | 514/336 |
| 5,070,211 | 12/1991 | Dekeyser et al. | 549/378 |
| 5,071,862 | 12/1991 | Friedlander et al. | 514/336 |
| 5,080,226 | 1/1992 | Hodakowski et al. | 206/205 |
| 5,094,853 | 3/1992 | Hagarty | 424/405 |
| 5,114,464 | 5/1992 | Davis et al. | 71/92 |
| 5,134,133 | 7/1992 | Covey et al. | 514/92 |
| 5,134,144 | 7/1992 | Brouwer et al. | 514/274 |
| 5,134,145 | 7/1992 | Brouwer et al. | 514/274 |
| 5,139,152 | 8/1992 | Hodakowski et al. | 206/524.7 |
| 5,169,430 | 12/1992 | Strunk et al. | 71/92 |
| 5,176,735 | 1/1993 | Bell | 504/168 |
| 5,215,747 | 6/1993 | Hairston et al. | 424/93 M |
| 5,222,595 | 6/1993 | Gouge et al. | 206/205 |
| 5,232,701 | 8/1993 | Ogawa et al. | 424/408 |
| 5,248,038 | 9/1993 | Hodakowski et al. | 206/205 |
| 5,253,759 | 10/1993 | Gouge et al. | 206/205 |
| 5,319,102 | 6/1994 | Davis et al. | 549/28 |
| 5,328,942 | 7/1994 | Akhtar et al. | 524/35 |
| 5,366,957 | 11/1994 | Cain et al. | 504/271 |

FOREIGN PATENT DOCUMENTS

| | | |
|---|---|---|
| 2848492 | 5/1993 | Australia. |
| 2083468 | 5/1993 | Canada. |
| 221630A1 | 5/1985 | Germany. |
| 260680A1 | 10/1988 | Germany. |
| 2095115 | 9/1982 | United Kingdom. |

OTHER PUBLICATIONS

Encyclopedia of Chemical Technology, Kirk–Othmer, Third Edition, vol. 10, John Wiley & Sons, Inc., 1980, p. 232.

Encyclopedia of Chemical Technology, Kirk–Othmer, Third Edition, vol. 20, John Wiley & Sons, Inc., 1982, pp. 207–230.

McCutcheon's, vol. 1: Emulsifiers & Detergents, 1994 North American Edition, McCutcheon Division, McPublishing Co., pp. 287–310.

McCutcheon's vol. 1: Emulsifiers & Detergents, 1994 International Edition, McCutcheon Division, McPublishing Co., pp. 257–280.

McCutcheon's vol. 2: Functional Materials, 1994 North American Edition, McCutcheon Division, The Manufacturing Confectioner Publishing Co., pp. 122–142.

McCutcheon's vol. 2: Functional Materials, 1994 International Division, McCutcheon Division, McPublishing Co., pp. 47–56.

Encyclopedia of Chemical Technology (Kirk–Othmer) vol. 7 "Defeamers" 3rd Ed. 1980.

*Primary Examiner*—S. Mark Clardy
*Attorney, Agent, or Firm*—Raymond D. Thompson

[57] ABSTRACT

Water-dispersible powder formulations used in connection with seed treatment and foliar treatment of plants provide excellent dust and rub-off control. The powder formulations comprise an active ingredient, a wetting agent, a dispersant, an anticaking agent, and an adhesion ingredient selected from the group consisting of a sodium salt of a polyacrylic acid, a sodium salt of maleic acid/acrylic acid copolymer, polyvinyl pyrrolidone, an alkylated polyvinyl pyrrolidone, and mixtures thereof. The wetting agent is present in an amount that is effective for enabling the powder formulation to be wettable by cold water. The dispersant is present in an amount that is effective for enabling the powder formulation to be dispersible in cold water. The anticaking agent is present in an amount that is effective for enabling the powder formulation to be re-suspendable in water. The adhesion ingredient is present in an amount that is effective for enabling the powder formulation to adhere to a plant leaf or seed. The powder formulations are especially suitable for containment in water soluble and/or water-dispersible bags or pouches, such use tending to render the active ingredient safer to handle and therefore better for consumers and the environment.

20 Claims, No Drawings

POWDER FORMULATION USEFUL FOR SEED TREATMENT AND FOLIAR TREATMENT OF PLANTS

TECHNICAL FIELD

Our present invention, in general, is directed to water-dispersible powder formulations used for treating seeds—especially wheat, barley, rye, triticale, oats, flax and canola—and for foliar treatment of plants.

More particularly, our invention is directed to water-dispersible powder formulations, used for treating seeds and for foliar treatment of plants, wherein the powder formulations are able to be contained within such water-soluble containers as water-soluble bags and pouches.

BACKGROUND ART

Compositions and formulations used for treating plants are well known. In this regard, U.S. Pat. No. 4,576,646 to Branco et al. (assigned to Seppic), U.S. Pat. No. 4,849,005 to Williams et al. and U.S. Pat. No. 5,300,127 to Williams (both assigned to Agricultural Genetics Company, Limited), U.S. Pat. No. 5,328,942 to Akhtar et al. (assigned to Uniroyal Chemical Company, Inc.) and United Kingdom Patent Application GB 2 095 115 A to Cannan et al. (assigned to FMC Corporation) are illustrative.

Formulations which are used for treating plants and which are contained within such water-soluble containers as water-soluble bags or pouches are also well known. Illustrative in this regard are U.S. Pat. Nos. 5,222,595 and 5,253,759 (both to Gouge et al.) and U.S. Pat. Nos. 5,080,226; 5,139,152 and 5,248,038 (all to Hodakowski et al.).

When a water-soluble container is used to contain a formulation, it is, of course, highly desirable that such a formulation include as little water as possible. Not surprisingly, lesser included amounts of water are a direct result of the use of a "powder" formulation.

To realize significant cost savings, many seed-treatment and foliar-treatment formulators would prefer to use powder formulations instead of conventional liquid formulations, if at all possible.

Yet, as those skilled in this particular art know full well, the use of powder formulations is not entirely problem-free.

For example, because certain leaf treatment or seed treatment powder formulations are known to initially disperse acceptably in room temperature (or warmer) water, those skilled in the art might encourage use of warmer water to achieve quicker, more uniform initial dispersion.

However, a vast majority of commercially-available seed treatment formulations are sold to applicators who combine the seed treatment powder formulation with water "in the field," frequently at times of the year when only cold water is available.

It therefore is desirable that there be available in the marketplace a powder formulation—such as for treatment of leaves or seeds—wherein the formulation, when in cold water, is able to readily and quickly initially disperse, preferably uniformly, with minimal energy being supplied for initial dispersion purposes.

Those skilled in the art can well appreciate that certain additional problems come to light when attempts are made to disperse in cold water a powder formulation contained within a water-soluble bag or pouch.

It would therefore also be desirable that there be available in the marketplace a powder formulation which, although contained within a water-soluble bag or pouch, nevertheless readily and quickly disperses, preferably uniformly, when combined with cold water.

Moreover, soon after a powder formulation is "let down" into water, dispersed and suspended, it may become necessary—for a variety of reasons—to use all or a portion of the suspension at some later time.

Moreover, those in the art know quite well that conventional leaf treatment and seed treatment powder formulations tend to settle out of the suspension and may undesirably "harden" soon after settling out, if not maintained in a suspended state, with the result being that it may become necessary to invest time and/or energy, often at considerable cost, to re-suspend or otherwise re-work a thus-hardened formulation.

Because maintaining conventional powder formulations in a suspended state for days, weeks or months is generally deemed to be impractical, it would be desirable to have available (to the user) powder formulations which have not been maintained in a suspended state for an extended period of time yet which nevertheless readily re-suspend, with minimal mixing action, whenever desired.

Also, leaf or seed treatment formulators tend to require that a uniform coating of "actives" and color (if used) be present on their leaves and seeds, wherein the leaf or seed treatment coating neither readily "dusts" (i.e. neither causes formation of dust or particles), nor easily washes off (of e.g. foliage), nor readily rubs off. It would accordingly be further desirable that there be available in the marketplace a powder formulation which is able to provide plants with a uniform coating that neither readily dusts, nor easily washes off, nor readily rubs off.

The foregoing desiderata, as well as other features and advantages of our invention will become more readily apparent to those skilled in the relevant art upon reading the following summary and detailed description.

SUMMARY DISCLOSURE OF INVENTION

Powder formulations disclosed herein are readily dispersible in liquid media such as water and are thereafter readily re-suspendable. Moreover, the powder formulations disclosed herein provide treated plant leaves and seeds with excellent dust control and rub-off control properties. The powder formulations comprise an active ingredient, a wetting agent, a dispersant, an anticaking agent, and an adhesion ingredient selected from the group consisting of a sodium salt of a polyacrylic acid, a sodium salt of maleic acid/acrylic acid copolymer, polyvinyl pyrrolidone, an alkylated polyvinyl pyrrolidone, and mixtures thereof. The wetting agent is present in an amount that is effective for enabling the powder formulation to be wettable by cold water. The dispersant is present in an amount that is effective for enabling the powder formulation to be dispersible in cold water. The anticaking agent is present in an amount that is effective for enabling the powder formulation to be re-suspendable in water. The adhesion ingredient is present in an amount that is effective for enabling the powder formulation to adhere to a plant leaf or seed. The powder formulations are especially suitable for containment in water soluble and/or water-dispersible bags or pouches, such use tending to render the active ingredient safer to handle and therefore better for consumers and the environment.

Our novel powder formulation may additionally include optional ingredients such as a plasticizer; an effervescent; a foam-control agent; a pigment agent or ingredient or a dye; a thickening agent; or a packaging film such as a water-soluble bag or pouch.

Moreover, as a result of our present invention, those powder formulations which further include a dye or other coloring agent or ingredient have been found to provide treated leaves and seeds with excellent uniform-color control.

BEST MODE FOR CARRYING OUT THE INVENTION

Our present invention is susceptible to embodiment in various forms. We have accordingly described our invention with respect to a number of examples which embody various principles of our invention.

It is, however, our intent that this disclosure be considered merely illustrative of our invention without limitation to the specific embodiments or examples discussed and described in detail herein. In the following detailed description, certain terms are used for purposes of conciseness and otherwise to elucidate the various aspects, features and advantages of our present invention. These terms are defined hereinbelow.

The term "active" as used herein shall, in general, be understood to mean any ingredient that is chemically active and/or biologically active in origin. In this regard, an "active" ingredient can be a single ingredient or a combination of ingredients; and the meaning of the term "active" shall be understood to include but not be limited to the following:

(1) such arthropodicidally-active compositions-of-matter as are disclosed and listed in U.S. Pat. No. 5,093,853 (to Hagarty);

(2) such bacterioidally-active compositions-of-matter as are disclosed in U.S. Pat. No. 4,182,716 (to Znotins et al.);

(3) such fungicidally-active compositions-of-matter as are disclosed in U.S. Pat. No. 4,182,716 (to Znotins et al.); U.S. Pat. No. 4,497,646 (to Rubio); U.S. Pat. No. 4,569,690 (to Brouwer et al.); U.S. Pat. Nos. 4,857,649 and 4,950,671 (both to Lai et al.); U.S. Pat. Nos. 4,966,912 and 5,061,716 (both to Relyea et al.); U.S. Pat. Nos. 5,039,332 and 5,071,862 (both to Friedlander et al.); and U.S. Pat. No. 5,215,747 (to Hairston et al.);

(4) such herbicidally-active compositions-of-matter as those disclosed in U.S. Pat. No. 4,497,646 (to Rubio); U.S. Pat. Nos. 4,569,690 and 4,927,451 (both to Brouwer et al.); U.S. Pat. No. 4,945,113 (to Nowakowski et al.); U.S. Pat. No. 4,966,910 (to Lai et al.); U.S. Pat. No. 4,979,982 (to Brouwer et al.); U.S. Pat. No. 4,981,508 (to Strunk et al.); U.S. Pat. No. 5,114,464 (to Davis et al.); U.S. Pat. No. 5,169,430 (to Strunk et al.); and U.S. Pat. No. 5,319,102 (to Davis et al.);

(5) such microbiologically-active compositions-of-matter as are disclosed in U.S. Pat. No. 5,215,747 (to Hairston et al.);

(6) such pesticidally-active compositions-of-matter as those disclosed in U.S. Pat. No. 4,839,349 (to Covey et al.); U.S. Pat. No. 5,010,068 (to Dekeyser et al.); U.S. Pat. No. 5,134,133 (to Covey et al.); and U.S. Pat. Nos. 5,134,144 and 5,134,145 (both to Brouwer et al.); and (7) such plant growth regulant-active compositions-of-matter as those disclosed in U.S. Pat. No. 4,319,033 (to Tsai et al.); U.S. Pat. No. 4,857,649 (to Lai et al.); U.S. Pat. No. 4,943,309 (to Bell); U.S. Pat. No. 5,039,332 (to Friedlander et al.); U.S. Pat. No. 5,070,211 (to Dekeyser et al.); and U.S. Pat. No. 5,176,735 (to Bell).

Other "active" ingredients useful in conjunction with our present invention are cited and otherwise set forth in the examples of this patent specification.

The term "adhesion ingredient" or "sticker mixture" connotes an ingredient or a mixture that is capable of causing a substance to adhere to a substrate. In this regard, the adhesion ingredient or sticker mixture of the invention functions as a carrier. Suitable adhesion ingredients include salts (of e.g. sodium, potassium or ammonium) of polyacrylic acid having an average molecular weight of 1,000–250,000 as well as salts (of e.g. sodium, potassium or ammonium) of acrylic/maleic copolymer.

The term "anticaking agent" shall, in general, be understood to mean a substance used to improve the integrity of a powder and to lessen the likelihood of the settling of a suspension. The term "anticaking agent" shall, more particularly, be understood to mean a substance which promotes overall structure, body or suspension properties, or which provides desired rheological properties to a final product. "Anticaking" agents include but are not limited to amorphous silicon dioxide and polyalkyl naphthalene sodium sulphate.

The term "coating," which includes the term "film," as used herein means a composition-of-matter which adheres to, or which covers, or is spread over a surface, wherein the term "surface" is referred to herein in its more general sense, namely, as a substrate.

The term "cold water," with respect to leaves and seeds, shall be understood to mean liquid water possessing a temperature of up to 20° C. In addition, the term "cold water," with respect to seeds only, shall be understood to mean liquid water possessing a temperature of up to 15° C. The term "very cold water," with respect to leaves and seeds, shall be understood to mean liquid water possessing a temperature of up to 10° C.; and the term "very cold water," with respect to seeds only, shall be understood to mean liquid water possessing a temperature of up to 5° C.

The term "colorant" or "coloring agent" shall be understood to include dyes and pigments.

The term "defoamer" or "foam-control" agent shall be understood to mean a substance that is used to reduce foaming. Foam-control agents are discussed at pages 928–945 in the *Kirk-Othmer Encyclopedia of Chemical Technology*, fourth edition, volume 7, published 1993 by John Wiley & Sons, Inc. Example of conventional "foam-control" agents include but are not limited to the group consisting of organic phosphates, silicone fluids with and without silica, sulphonated oils, alcohols, polyols, acetylenic glycol, hydrocarbon oil, fatty acids and esters, and 2-octanol.

The term "dispersant" or "dispersing agent" as used herein connotes a surface-active agent which is added to liquid suspending media to promote the homogeneous suspension and separation of typically extremely fine solid particles, often of colloidal size, throughout the liquid suspending media. Dispersants suitable for purposes of our present invention are listed in *McCutcheon's Functional Materials*, at pages 122–142 of the North American Edition (1994), as well as in *McCutcheon's Functional Materials*, at pages 47–56 of the International Edition (1994), both published by MC Publishing Company (McCutcheon Division) of Glen Rock, N.J. In this regard, suitable dispersants include but are not limited to nonionic block copolymer of polyethylene oxide and polypropylene oxide, alkoxylated linear alcohols, ethoxylated alkylphenols, ethoxylated fatty esters, glyceryl esters, polyaromatic sulfonate, sulfonates of condensed naphthalenes, sodium alkylaryl sulfonates (including sodium dodecylbenzene sulfonate, sodium butyl naphthalene sulfonate, sodium naphthalene sulfonate formaldehyde polymer, sodium salts of polymerized alkyl naphthalene sulfonate, potassium salts of polymerized alkyl naphthalene sulfonate), polyvinyl pyrrolidone, lignosulfonates (including nonionic surfactant and sodium lignosulfonate blends, anionic surfactant and sodium lignosulfonate blends, modified sodium-calcium lignosulfonate, highly purified partially desulfonated ammonium lignosulfonate and sugar-free ammonium lignosulfonate) and sulfosuccinates (including dioctyl sodium sulfosuccinate, ditridecyl sodium sulfosuccinate and dicyclohexyl sodium sulfosuccinate).

The term "dye" as used herein, in general, connotes either a coloring ingredient, natural or otherwise, such as an organic colorant that is derived from a petroleum-based intermediate to impart permanent color to a substrate.

The term "effervescent" as used herein comprises an alkaline carbonate component or ingredient as well as a solid and weak acid component or ingredient. In this regard, the alkaline carbonate can be derived either from an alkali metal (especially sodium or potassium), or from an alkaline-earth metal (especially calcium or magnesium), or from an ammonium or organoammonium group or cation (carbonate derived from a primary, secondary or tertiary amine, or from a quaternary ammonium cation), but is preferably derived from an alkali metal, especially sodium or potassium; and the solid and weak acid is either a carboxylic or polycarboxylic acid, or a phosphoric or phosphonic acid, or one of their salts or esters containing an acidic functional group.

The term "film" as used herein connotes either a veneer; or a relatively fine or thin skin; or a delicate coating on a surface; or an outer membrane; or an ultrafine layer on a substrate.

The term "pigment" as used herein means a composition-of-matter, usually in the form of a dry powder, which imparts color to another composition-of-matter or to a mixture.

The term "plasticizer" as used herein connotes a substance which is added to a suspension to enhance the flexibility of a coating or film on a substrate, for example, a seed surface or a plant surface such as a leaf. Plasticizers suitable for purposes of our present invention are listed in *McCutcheon's Functional Materials*, at pages 223–230 of the North American Edition (1994), as well as in *McCutcheon's Functional Materials*, at pages 87–88 of the International Edition (1994), both published by The Manufacturing Confectioner Publishing Co. (McCutcheon Division) of Glen Rock, N.J. In this regard, suitable plasticizers include but are not limited to hydrocarbon oil having a boiling point of at least 150° C., vegetable oil, polyoxypropylene-polyoxyethylene block polymers, propylene glycol, polypropylene glycol, polyethylene glycol, polyethylene sorbitan monolaurate, and polyether glycol.

The term "powder" shall be understood to mean a finely-divided solid composition that may contain a minor amount of at least one liquid ingredient.

The term "room temperature" shall be understood to mean a temperature of from 21 degrees Celsius to 25° C.

The term "warm water" shall be understood to mean water possessing a temperature which is greater than room temperature.

The term "wetting agent" shall be understood to mean liquid-soluble substance that promotes the spreading of the liquid, at the air-liquid interface. This is particularly evident at the surface of water insoluble ingredients such as the Active Ingredient and Pigment.

DETAILED DESCRIPTION OF EXAMPLES

The following examples are set forth to describe more particularly, to those skilled in the art, the principles and practice of our invention. In this regard, the examples are not intended to limit our invention. Rather, the examples are intended to be merely illustrative of certain aspects of our various preferred embodiments.

In the following examples, there are presented powder formulations which include an active ingredient, a wetting agent, a dispersant, an anticaking agent, and an adhesion ingredient selected from the group consisting of a sodium salt of a polyacrylic acid, a sodium salt of maleic acid/ acrylic acid copolymer, polyvinyl pyrrolidone, an alkylated polyvinyl pyrrolidone, and mixtures thereof.

The wetting agent is present in an amount that is effective for enabling the powder formulation to be wettable by cold water.

The dispersant is present in an amount that is effective for enabling the powder formulation to be dispersible in cold water.

The anticaking agent is present in an amount that is effective for enabling the powder formulation to be re-suspendable in water.

Some of the above-identified adhesion ingredients also function, to some degree, as a re-suspending agent, and thus are also effective for enabling the powder formulation to be re-suspendable in water.

The adhesion ingredient is present in an amount that is effective for enabling the powder formulation to adhere to a plant leaf or seed.

The powder formulations are especially suitable for containment in water soluble and/or water-dispersible bags or pouches, such use tending to render the active ingredient safer to handle and therefore better for consumers and the environment.

Our novel powder formulation may additionally include optional ingredients such as a plasticizer, an effervescent, a foam-control agent, a pigment agent or ingredient or a dye, a thickening agent or ingredient, and a packaging film.

Moreover, as a result of our present invention, those powder formulations which further include a dye or other coloring agent or ingredient have been found to provide treated leaves and seeds with excellent uniform-color control.

Procedures To Produce Powder Formulations

Dry powder ingredients as well as pigment were combined in a commercially-available mixing unit (either a "V" blender, or ribbon-type blender, or other suitable blender) and blended until the mixture was homogeneous. (The resultant powder mixture can optionally further be pulverized, using a suitable grinder such as a "hammermill" type grinder, to a desired particle size of 10–100 microns.) To this powder mixture were added desired liquid ingredients. The final mixture was then blended until homogeneous and then ground, to produce particles having a desired particle size of 1–100 microns.

In the following examples, ingredients selected were dry and did not contain any so-called "free" water or any other solvent which—if otherwise present—would deleteriously affect a water-soluble bag or pouch into which the powder formulation of the invention is placed.

The powder formulation of the invention can advantageously therefore be packaged in water soluble or water dispersible pouches or bags wherein such a bag may for example be made either of polyethylene oxide or methylcellulose or polyvinyl acetate or polyvinyl alcohol. (For example, 88 wt.-% hydrolyzed polyvinyl acetate, cold water soluble.) The size of such a pouch or bag can range from 10 grams to 25 kilograms. Additional packaging films suitable for purposes of our invention are set forth at pages 207–230 in the *Kirk-Othmer Encyclopedia of Chemical Technology*, third edition, volume 20, published 1982 by John Wiley & Sons, Inc., and at page 774 of *Kirk-Othmer Encyclopedia Of Chemical Technology*, fourth edition, volume 10, published 1993.

General and preferred ranges of ingredients are set forth below in Table I.

TABLE I

General and Preferred Ranges of Ingredients

| Ingredients | General Range, Weight Percentage | Preferred Range, Weight Percent |
| --- | --- | --- |
| Active Ingredient | 0.1–90 | 1–70 |
| Adhesion Ingredient | 1–50 | 5–30 |
| Dispersant | 0.1–50 | 1–35 |
| Wetting Agent | 0.1–20 | 0.5–6 |
| Anticaking Agent | 0.1–20 | 0.5–5 |
| Pigment | 0–50 | 0–30 |
| Effervescent* | 0–40 | 0–20 |
| Plasticizer | 0–20 | 0–12 |
| Foam-Control Agent | 0–20 | 0–5 |

*Note: Effervescent = solid acid + carbonate.

EXAMPLE 1

One Such Powder Formulation Illustrative of the Invention

The ingredients of Example 1 are set forth below in Table II.

TABLE II

| Ingredients | Weight Percent |
| --- | --- |
| Adhesion Ingredient | 32.28 |
| Pigment | 23.33 |
| Dispersant | 20.00 |
| Active Ingredient | 13.89 |
| Plasticizer | 8.00 |
| Foam-Control Agent | 1.50 |
| Wetting Agent | 1.00 |
| Anticaking Agent | 1.00 |

In example 1, the adhesion ingredient present at 32.28 weight percent ("wt-%") is a sodium salt of polyacrylic acid, having an average molecular weight of 8000, and is a dry powder having a flash point temperature of >100° C. The pigment ingredient present at 23.33 wt-% is 2-naphthalenecarboxylic acid 3-hydroxy-4-[(4-methyl-2-sulfophenyl)azo]-calcium salt. (Color Index pigment red 57:1.) The dispersant ingredient present at 20.00 wt-% is a linear alkylbenzene sulfonate. The active ingredient present at 13.89 wt-% is $\alpha$[2-(4-chlorophenyl)ethyl-$\alpha$-(1,1-dimethylethhyl)-1H-1,2,4-triazole-1-ethanol, known as tebuconazole. The plasticizer present at 8.00 wt-% is polypropylene glycol, having a weight average molecular weight of 4000. The foam-control agent present at 1.50 wt-% is a blend of silicone compound, polyethylene glycol 600 dioleate, and silica derivatives. The wetting agent present at 1.00 wt-% is a sodium salt of an alkylated naphthalene sulfonate. The anticaking agent present at 1.00 wt-% is an amorphous silicone dioxide.

EXAMPLE 2

Another Powder Formulation Illustrative Of The Invention

In this example, procedures (set forth above) to produce powder formulations were followed, using the ingredients set forth in Example 1.

The ingredients of Example 2 are set forth below in Table III.

TABLE III

| Ingredients | Weight Percent |
| --- | --- |
| Adhesion Ingredient | 32.27 |
| Dispersant | 20.00 |
| Plasticizer | 16.00 |
| Pigment | 14.00 |
| Active Ingredient | 7.73 |
| Wetting Agent | 6.00 |
| Anticaking Agent | 2.50 |
| Foam-Control Agent | 1.50 |

In Example 2, the adhesion ingredient, the plasticizer and the active ingredient were the same as used in Example 1. The pigment that was used is designated as a Color Index ("CI") Pigment Red 57:1. The dispersant was a blend of anionic surfactant and sodium lignosulfonate. The wetting agent was an octylphenoxypolyethoxyethanol having an average degree of ethoxylation of 9–10 moles of ethylene oxide. The anticaking agent was an amorphous silicon dioxide. The foam-control agent was a compounded silicone fluid.

EXAMPLE 3

Yet Another Powder Formulation Illustrative of the Invention

In this example, procedures (set forth above) to produce powder formulations were followed, and the ingredients which were utilized are set forth below.

The ingredients of Example 3 are set forth below in Table IV.

TABLE IV

| Ingredients | Weight Percent |
| --- | --- |
| Adhesion Ingredient | 63.00 |
| Plasticizer | 14.95 |
| Pigment | 10.00 |
| Dispersant | 5.00 |
| Wetting Agent | 3.00 |
| Active Ingredient | 1.55 |
| Foam-Control Agent | 1.50 |
| Anticaking Agent | 1.00 |

In Example 3, the adhesion ingredient, the plasticizer, the active ingredient, and the anticaking agent are described above in connection with Example 1. The pigment that was used is designated as a commercially-available CI Pigment Blue 15:1. The wetting agent is an octylphenol ethoxylate having an average degree of ethoxylation of 9–10 moles of ethylene oxide. The dispersant is an alkyl sulfate. The foam-control agent is described in Example 2.

EXAMPLE 4

Yet Another Powder Formulation Illustrative of the Invention

In this example, procedures (set forth above) to produce powder formulations were followed, and the ingredients which were utilized are set forth below.

The ingredients of Example 4 are set forth below in Table V.

TABLE V

| Ingredients | Weight Percent |
| --- | --- |
| Active Ingredient | 51.55 |
| Adhesion Ingredient | 27.60 |
| Plasticizer | 8.00 |
| Dispersant | 6.00 |
| Pigment | 2.55 |
| Foam-Control Agent | 1.50 |
| Anticaking Agent | 1.00 |
| Wetting Agent | 1.00 |

In Example 4, the active ingredient, commercially available from Uniroyal Chemical Company, Inc., of Middlebury, Conn., is 5,6-Dihydro-2-methyl-N-phenyl-1,4-oxathiin-3-carboxanilide, also known as carbathiin or carboxin. The adhesion ingredient, the anticaking agent, the pigment, the wetting agent, and the dispersant are described above in connection with Example 1. The plasticizer is polyethylene glycol having a weight average molecular weight of 400. The foam-control agent is described in Example 1.

EXAMPLE 5

Yet Another Powder Formulation Illustrative of the Invention

In this example, procedures (set forth above) to produce powder formulations were followed, and the ingredients which were utilized are set forth below.

The ingredients of Example 5 are set forth below in Table VI.

TABLE VI

| Ingredients | Weight Percent |
| --- | --- |
| Active Ingredient | 51.55 |
| Adhesion Ingredient | 27.60 |
| Plasticizer | 8.00 |
| Dispersant | 6.00 |
| Pigment | 2.55 |
| Foam-Control Agent | 1.50 |
| Anticaking Agent | 1.00 |
| Wetting Agent | 1.00 |

In Example 5, the adhesion ingredient, the pigment, the wetting agent, the dispersant, the anticaking agent, and the foam-control agent are described above in connection with Example 1. The active ingredient is described above in connection with Example 4. The plasticizer is a commercially-available polyoxyethylene sorbitan monolaurate which is supplied by ICI Americas, Inc.

EXAMPLE 6

Still Another Powder Formulation Illustrative of the Invention

In this example, procedures (set forth above) to produce powder formulations were followed, and the ingredients which were utilized are set forth below.

The ingredients of Example 6 are set forth below in Table VII.

TABLE VII

| Ingredients | Weight Percent |
| --- | --- |
| Active Ingredient | 51.65 |
| Adhesion Ingredient | 27.60 |
| Plasticizer | 8.00 |
| Dispersant | 6.00 |
| Pigment | 2.00 |
| Foam-Control Agent | 1.50 |
| Wetting Agent | 1.45 |
| Anticaking Agent | 1.00 |

In Example 6, the active ingredient is 1-[(6-chloro-3-pyridinyl)methyl]-N-nitro-2-imidazolidinimine, also known as imidacloprid. The adhesion ingredient is a sodium salt of acrylic/maleic copolymer having a weight average molecular weight of 70,000. The plasticizer, the pigment, the dispersant, the anticaking agent, and the foam-control agent are described above in connection with Example 1. The wetting agent is described in Example 2.

EXAMPLE 7

Yet Another Powder Formulation Illustrative of the Invention

In this example, procedures (set forth above) to produce powder formulations were followed, and the ingredients which were utilized are set forth below.

The ingredients of Example 7 are set forth below in Table VIII.

TABLE VIII

| Ingredients | Weight Percent |
| --- | --- |
| Active Ingredient | 55.75 |
| Adhesion Ingredient | 27.00 |
| Dispersant | 6.00 |
| Plasticizer | 3.00 |
| Pigment | 2.75 |
| Foam-Control Agent | 2.00 |
| Wetting Agent | 2.00 |
| Anticaking Agent | 1.00 |

In Example 7, the adhesion ingredient, the plasticizer, the pigment, the dispersant, the anticaking agent, and the foam-control agent are all described in Example 1. The active ingredient is described in Example 4. The wetting agent is described in Example 2.

EXAMPLE 8

Still Another Powder Formulation Illustrative of the Invention

In this example, procedures (set forth above) to produce powder formulations were followed, and the ingredients which were utilized are set forth below.

The ingredients of Example 8 are set forth below in Table IX.

TABLE IX

| Ingredients | Weight Percent |
| --- | --- |
| Active Ingredient | 55.75 |
| Adhesion Ingredient | 27.00 |
| Dispersant | 6.00 |

TABLE IX-continued

| Ingredients | Weight Percent |
| --- | --- |
| Plasticizer | 3.00 |
| Pigment | 2.75 |
| Foam-Control Agent | 2.00 |
| Wetting Agent | 2.00 |
| Anticaking Agent | 1.00 |
| Packaging Film | 0.50 |

In Example 8, the adhesion agent, the plasticizer, the active ingredient, the pigment, the wetting agent, the dispersant, the anticaking agent, and the foam-control agent are all as described in Example 7. The packaging film is polyvinyl alcohol film.

EXAMPLE 9

Yet Another Powder Formulation Illustrative of the Invention

In this example, procedures (set forth above) to produce powder formulations were followed, and the ingredients which were utilized are set forth below.

The ingredients of Example 9 are set forth below in Table X.

TABLE X

| Ingredients | Weight Percent |
| --- | --- |
| Active Ingredient | 51.55 |
| Adhesion Ingredient | 27.60 |
| Plasticizer | 8.00 |
| Dispersant | 6.00 |
| Pigment | 2.55 |
| Foam-Control Agent | 1.50 |
| Anticaking Agent | 1.00 |
| Wetting Agent | 1.00 |

In Example 9, the adhesion ingredient, the pigment, the wetting agent, the dispersant, the anticaking agent, and the foam-control agent are described in Example 1. The active ingredient is described above in connection with Example 4. The plasticizer is propylene glycol.

EXAMPLE 10

Yet Another Powder Formulation Illustrative of the Invention

In this example, procedures (set forth above) to produce powder formulations were followed, and the ingredients which were utilized are set forth below.

The ingredients of Example 10 are set forth below in Table XI.

TABLE XI

| Ingredients | Weight Percent |
| --- | --- |
| Active Ingredient | 51.55 |
| Adhesion Ingredient | 27.60 |
| Plasticizer | 8.00 |
| Dispersant | 6.00 |
| Pigment | 2.55 |
| Foam-Control Agent | 1.50 |
| Anticaking Agent | 1.00 |
| Wetting Agent | 1.00 |

In Example 10, the adhesion ingredient, the active ingredient, the pigment, the dispersant, the anticaking agent, and the foam-control agent are described in Example 9. The plasticizer is a polyoxypropylene-polyoxyethylene block polymer. The wetting agent is an anionic surfactant.

EXAMPLE 11

Yet Another Powder Formulation Illustrative Of The Invention

In this example, procedures (set forth above) to produce powder formulations were followed, and the ingredients which were utilized are set forth below.

The ingredients of Example 11 are set forth below in Table XII.

TABLE XII

| Ingredients | Weight Percent |
| --- | --- |
| Active Ingredient | 51.55 |
| Adhesion Ingredient | 27.60 |
| Plasticizer | 8.00 |
| Dispersant | 6.00 |
| Pigment | 2.55 |
| Foam-Control Agent | 1.50 |
| Anticaking Agent | 1.00 |
| Wetting Agent | 1.00 |

In Example 11, the adhesion ingredient, the active ingredient, the pigment, the wetting agent, the dispersant, the anticaking agent, and the foam-control agent are described above in connection with Example 10.

The plasticizer is tri(propylene glycol), 97 wt.-%, supplied by the Aldrich Chemical Company of Milwaukee, Wis.

EXAMPLE 12

Yet Another Powder Formulation Illustrative of the Invention

In this example, procedures (set forth above) to produce powder formulations were followed, and the ingredients which were utilized are set forth below.

The ingredients of Example 12 are set forth below in Table XIII.

TABLE XIII

| Ingredients | Weight Percent |
| --- | --- |
| Active Ingredient | 51.55 |
| Adhesion Ingredient | 27.60 |
| Plasticizer | 8.00 |
| Dispersant | 6.00 |
| Pigment | 2.55 |
| Foam-Control Agent | 1.50 |
| Anticaking Agent | 1.00 |
| Wetting Agent | 1.00 |

In Example 12, the adhesion ingredient, the active ingredient, the pigment, the wetting agent, the dispersant, the anticaking agent, and the foam-control agent are described in Example 10. The plasticizer is polyether glycol Terathane 2900, also supplied by Aldrich Chemical Co.

EXAMPLE 13

Yet Another Powder Formulation Illustrative of the Invention

In this example, procedures (set forth above) to produce powder formulations were followed, and the ingredients which were utilized are set forth below.

The ingredients of Example 13 are set forth below in Table XIV.

TABLE XIV

| Ingredients | Weight Percent |
| --- | --- |
| Active Ingredient | 51.55 |
| Adhesion Ingredient | 27.60 |
| Plasticizer | 8.00 |
| Dispersant | 6.00 |
| Pigment | 2.55 |
| Foam-Control Agent | 1.50 |
| Anticaking Agent | 1.00 |
| Wetting Agent | 1.00 |

In Example 13, the adhesion ingredient, the active ingredient, the pigment, the wetting agent, the dispersant, the anticaking agent, and the foam-control agent are described in Example 10. The plasticizer is polyether glycol Terathane 650, also supplied by Aldrich Chemical Co.

EXAMPLE 14

Yet Another Powder Formulation Illustrative Of The Invention

In this example, procedures (set forth above) to produce powder formulations were followed, and the ingredients which were utilized are set forth below.

The ingredients of Example 14 are set forth below in Table XV.

TABLE XV

| Ingredients | Weight Percent |
| --- | --- |
| Active Ingredient | 51.55 |
| Adhesion Ingredient | 27.60 |
| Plasticizer | 8.00 |
| Dispersant | 6.00 |
| Pigment | 2.55 |
| Foam-Control Agent | 1.50 |
| Anticaking Agent | 1.00 |
| Wetting Agent | 1.00 |

In Example 14, the active ingredient, the pigment, the wetting agent, the dispersant, the anticaking agent, and the foam-control agent are described in Example 10. The adhesion ingredient is a sodium salt of polyacrylic acid having a weight average molecular weight of 30,000. The plasticizer is described in Example 1.

EXAMPLE 15

Yet Another Powder Formulation Illustrative of the Invention

In this example, procedures (set forth above) to produce powder formulations were followed, and the ingredients which were utilized are set forth below.

The ingredients of Example 15 are set forth below in Table XVI.

TABLE XVI

| Ingredients | Weight Percent |
| --- | --- |
| Active Ingredient | 51.55 |
| Adhesion Ingredient | 27.60 |
| Plasticizer | 8.00 |
| Dispersant | 6.00 |

TABLE XVI-continued

| Ingredients | Weight Percent |
| --- | --- |
| Pigment | 2.55 |
| Foam-Control Agent | 1.50 |
| Anticaking Agent | 1.00 |
| Wetting Agent | 1.00 |

In Example 15, the active ingredient, the pigment, the wetting agent, the dispersant, the anticaking agent, and the foam-control agent are described above in connection with Example 10. The adhesion ingredient is a sodium salt of polyacrylic acid having a weight average molecular weight of 2,100. The plasticizer is described in Example 1.

EXAMPLE 16

Yet Another Powder Formulation Illustrative of the Invention

In this example, procedures (set forth above) to produce powder formulations were followed, and the ingredients which were utilized are set forth below.

The ingredients of Example 16 are set forth below in Table XVII.

TABLE XVII

| Ingredients | Weight Percent |
| --- | --- |
| Active Ingredient | 56.70 |
| Adhesion Ingredient | 27.00 |
| Foam-Control Agent | 5.50 |
| Dispersant | 5.00 |
| Pigment | 2.80 |
| Anticaking Agent | 1.20 |
| Wetting Agent | 1.00 |

In Example 16, the adhesion ingredient, the active ingredient, the pigment, the wetting agent, the dispersant, and the anticaking agent are described above in connection with Example 10. The foam-control agent is described in Example 2.

EXAMPLE 17

Yet Another Powder Formulation Illustrative of the Invention

In this example, procedures (set forth above) to produce powder formulations were followed, and the ingredients which were utilized are set forth below.

The ingredients of Example 17 are set forth below in Table XVIII.

TABLE XVIII

| Ingredients | Weight Percent |
| --- | --- |
| Active Ingredient | 56.70 |
| Adhesion Ingredient | 27.00 |
| Dispersant | 9.00 |
| Pigment | 2.80 |
| Foam-Control Agent | 1.50 |
| Anticaking Agent | 1.20 |
| Wetting Agent | 1.00 |

In Example 17, the adhesion ingredient, the active ingredient, the pigment, the wetting agent, the dispersant, and the anticaking agent all are described above in connection with Example 10. The foam-control agent is described in Example 2.

EXAMPLE 18

Yet Another Powder Formulation Illustrative of the Invention

In this example, procedures (set forth above) to produce powder formulations were followed, and the ingredients which were utilized are set forth below.

The ingredients of Example 18 are set forth below in Table XIX.

TABLE XIX

| Ingredients | Weight Percent |
| --- | --- |
| Active Ingredient | 56.70 |
| Adhesion Ingredient | 27.00 |
| Dispersant | 9.00 |
| Plasticizer | 4.00 |
| Pigment | 2.80 |
| Foam-Control Agent | 1.50 |
| Anticaking Agent | 1.20 |
| Wetting Agent | 1.00 |

In Example 18, the adhesion ingredient, the active ingredient, the pigment, the wetting agent, the dispersant, and the anticaking agent are described in Example 10. The plasticizer is a hydrocarbon having a boiling point >310° C. The foam-control agent is described in Example 2.

EXAMPLE 19

Yet Another Powder Formulation Illustrative of the Invention

In this example, procedures (set forth above) to produce powder formulations were followed, and the ingredients which were utilized are set forth below.

The ingredients of Example 19 are set forth below in Table XX.

TABLE XX

| Ingredients | Weight Percent |
| --- | --- |
| Active Ingredient | 61.27 |
| Adhesion Ingredient | 21.33 |
| Plasticizer | 5.00 |
| Pigment | 3.03 |
| Dispersant No. 1 | 3.00 |
| Foam-Control Agent | 2.00 |
| Wetting Agent | 2.00 |
| Anticaking Agent | 1.00 |
| Packaging Film | 0.86 |
| Dispersant No. 2 | 0.50 |

In Example 19, the adhesion agent, the pigment, and the packaging film are described in Example 6. The plasticizer is described in Example 1. The active ingredient, the wetting agent, and the anticaking agent are described in Example 8. Dispersant No. 1 is a sodium lignosulfonate. Dispersant No. 2 is a sodium salt of polymethacrylic acid. The foam-control agent is a blend of hydrocarbons, fatty acid derivatives, and surface active agents from Drew Chemical Limited of Ajax, Ontario, Canada.

EXAMPLE 20

Yet Another Powder Formulation Illustrative of the Invention

In this example, procedures (set forth above) to produce powder formulations were followed, and the ingredients which were utilized are set forth below.

The ingredients of Example 20 are set forth below in Table XXI.

TABLE XXI

| Ingredients | Weight Percent |
| --- | --- |
| Active Ingredient | 51.55 |
| Adhesion Ingredient | 27.60 |
| Plasticizer | 8.00 |
| Dispersant | 6.00 |
| Pigment | 2.55 |
| Foam-Control Agent | 1.50 |
| Anticaking Agent | 1.00 |
| Wetting Agent | 1.00 |

In Example 20, the adhesion ingredient, the pigment, the anticaking agent, and the foam-control agent are described above in connection with Example 6. The plasticizer is a purified canola oil. The active ingredient and the wetting agent are described above in connection with Example 5. The dispersant is described in Example 3.

EXAMPLE 21

Yet Another Powder Formulation Illustrative of the Invention

In this example, procedures (set forth above) to produce powder formulations were followed, and the ingredients which were utilized are set forth below.

The ingredients of Example 21 are set forth below in Table XXII.

TABLE XXII

| Ingredients | Weight Percent |
| --- | --- |
| Active Ingredient | 51.55 |
| Adhesion Ingredient | 27.60 |
| Plasticizer | 7.80 |
| Dispersant | 6.00 |
| Pigment | 2.55 |
| Foam-Control Agent | 1.50 |
| Anticaking Agent | 1.00 |
| Wetting Agent | 1.00 |
| Thickening Agent | 0.20 |

In Example 21, the adhesion ingredient, the active ingredient, the pigment, the wetting agent, the dispersant, the anticaking agent, and the foam-control agent are described above in connection with Example 4. The plasticizer is described above in connection with Example 1. The thickening agent is xanthan gum.

EXAMPLE 22

Yet Another Powder Formulation Illustrative of the Invention

In this example, procedures (set forth above) to produce powder formulations were followed, and the ingredients which were utilized are set forth below.

The ingredients of Example 22 are set forth below in Table XXIII.

TABLE XXIII

| Ingredients | Weight Percent |
| --- | --- |
| Active Ingredient | 51.55 |
| Adhesion Ingredient | 24.08 |

TABLE XXIII-continued

| Ingredients | Weight Percent |
| --- | --- |
| Plasticizer | 8.00 |
| Dispersant | 6.00 |
| Pigment | 2.55 |
| Sodium Carbonate | 1.60 |
| Citric Acid | 1.92 |
| Foam-Control Agent | 1.50 |
| Anticaking Agent | 1.00 |
| Packaging film (water soluble or water dispersible film) | 0.80 |
| Wetting Agent | 1.00 |

In Example 22, the adhesion ingredient, the active ingredient, the pigment, the wetting agent, the dispersant, the anticaking agent, and the foam-control agent are described in Example 4. The plasticizer is described in Example 1. The packaging film is described in Example 19.

Results

The above-described powders were then easily let down in water (in general at a weight ratio of water to powder of 7:1) and the resultant aqueous suspensions were used to coat seeds. The thus-coated seeds were observed to be smooth, shiny and dyed evenly red or blue.

Dustiness of the coated seeds was measured by known light-scattering methods. Procedures used to determine seed dustiness were as follows. After being air-dried, 100 grams of thus-coated seed were allowed to fall 43 centimeters (17 inches) to the floor, inside a closed box. The resulting dust cloud was illuminated above the dropped seed by a light source, and the reflected light from the resultant, air-suspended dust particles was converted to an applied voltage by a photovoltaic cell. The resultant voltage was monitored by a computer and a strip chart. The intensity of reflected light was then converted to the amount of dust generated by the dropped seed. Wheat and Barley seed were treated with various formulations. Dust generated was measured as shown in Tables XXIV and XXV. Table XXIV indicates the amount of dust generated by each seed treatment or lack thereof. Seed type: Scepter durum wheat.

TABLE XXIV

| Type of Seed Treatment | Dust Generated (mg/m$^3$) |
| --- | --- |
| Untreated (Scepter durum wheat) | 4.8 |
| Composition of Example 1 | 1.5 |
| Composition of Example 2 | 1.0 |
| Composition of Example 3 | 0.4 |
| Composition of Example 4 | 1.2 |
| Composition of Example 5 | 1.3 |
| Composition of Example 6 | 0.5 |
| Composition of Example 7 | 0.8 |
| Composition of Example 8 | 0.7 |
| Composition of Example 9 | 1.2 |
| Composition of Example 10 | 0.8 |
| Composition of Example 11 | 1.5 |
| Composition of Example 12 | 1.3 |
| Composition of Example 13 | 0.9 |
| Composition of Example 14 | 0.7 |
| Composition of Example 15 | 1.6 |
| Composition of Example 16 | 1.6 |
| Composition of Example 17 | 1.2 |
| Composition of Example 18 | 1.2 |
| Composition of Example 19 | 1.4 |

TABLE XXV

| Type of Seed Treatment | Dust Generated (mg/m$^3$) |
| --- | --- |
| Untreated (Harrington barley) | 2.8 |
| Composition of Example 1 | 1.2 |
| Composition of Example 2 | 1.2 |
| Composition of Example 3 | 0.7 |
| Composition of Example 4 | 1.4 |
| Composition of Example 5 | 1.2 |
| Composition of Example 6 | 1.2 |
| Composition of Example 7 | 1.0 |
| Composition of Example 8 | 1.1 |
| Composition of Example 9 | 1.3 |
| Composition of Example 10 | 1.1 |
| Composition of Example 11 | 1.7 |
| Composition of Example 12 | 1.5 |
| Composition of Example 13 | 1.5 |
| Composition of Example 14 | 1.7 |
| Composition of Example 15 | 1.0 |
| Composition of Example 16 | 1.8 |
| Composition of Example 17 | 1.2 |
| Composition of Example 18 | 1.2 |
| Composition of Example 19 | 2.0 |

Additional actives suitable for purposes of our invention include β-(4-chlorophenoxy)-α-(1,1-dimethylethyl)-1H-1,2,4-triazole-1-ethanol, also known as triadimenol; Rhizobia sp.; *Penicillium bilajii*; *Bacillus subtillis*; 2,3-dihydro-5,6-dimethyl-1,4-dithiin-1,1,4,4-tetraoxide, also known as dimethipin; tetraethylthiuram disulfide, also known as thiram; 2-(4-thiazolyl)benzimidazole, also known as thiabendazole; [1α,3α(Z)]-(±)-(2-methyl[1,1'-biphenyl]-3-yl) methyl 3-(2-chloro-3,3,3-trifluoro-1- propenyl)-2,2-dimethylcyclopropanecarboxylate, also known as bifenthrin; 1,2,3,4,5,6-hexachlorocyclohexane, gamma-isomer, also known as lindane; N-(2,6-dimethylphenyl)-N-(methoxyacetyl)-alanine methyl ester, also known as metalaxyl; 1-[(6-chloro-3-pyridinyl)methyl]-N-nitro-2-imidazolidinimine, also known as imidacloprid; and α-butyl-α'-(4-chlorophenyl)-1H-1,2,4-triazole propanenitrile, also known as myclobutanil.

Additional adhesion ingredients suitable for purposes of our present invention include but are not limited to polyvinyl pyrrolidone, the sodium salt of sulfonated polystyrene, vinyl pyrrolidone/vinyl acetate copolymers, polyamide resins, cationic cellulose and Polyquaternium-10.

Additional anticaking agents suitable for purposes of the present invention—in addition to fumed silica (untreated or treated)—include but are not limited to synthetic calcium silicate, sodium polyalkyl naphthalene sulfonate, microcrystalline cellulose, and sodium aluminosilicate.

Additional plasticizers suitable for purposes of our present invention include but are not limited to polyalkyl polysiloxane copolymer, polyoxyalkene silicone copolymer, and silicone-dimethyl polysiloxane. Additional thickening agents suitable for purposes of our present invention include but are not limited to fumed silica, the sodium salt of polyacrylic acid, sodium carboxymethyl cellulose, organoclay/polymer blends, microcrystalline cellulose, methyl cellulose, magnesium silicate, poly(methyl vinyl ether/maleic) anhydride, potassium/sodium alginate, hydroxypropyl cellulose, and magnesium aluminum silicate.

Additional wetting agents suitable for purposes of our present invention include but are not limited to the sodium salt of alkylated naphthalene sulfonate, formaldehyde polymer, alkanolamides, alkylaryl sulfonates, sulfonate derivatives, fluorocarbon-based surfactants, lignin and lignin derivatives, olefin sulfonates, quaternary surfactants, sulfates of ethoxylated alcohols, sulfonates of condensed naphthalenes and tridecylbenzenes and sulfosuccinates.

Preferred dispersants are selected from the group consisting of block polymers, alkylphenol ethoxylates, ethoxylated alcohols, ethoxylated alkylphenols, polyacrylic acid, propoxylated alkylphenols, sulfonated ethoxylated alkylphenols, lignin & lignin derivatives, tridecyl & dodecyl benzene sulfonic acid, and mixtures thereof.

Preferred packaging-film ingredients include methyl cellulose; polyethylene oxide; polyvinyl alcohol; and starch. (The weight percentage of a film depends upon the desired density and thickness of the film.)

Preferred solid and weak acid ingredients are selected from the group consisting of citric acid, tartaric acid, succinic acid, malic acid, malonic acid, and mixtures thereof.

Preferred alkaline carbonate ingredients are selected from the group consisting of sodium carbonate, potassium carbonate, sodium bicarbonate, potassium bicarbonate, and mixtures thereof.

What has been described herein is a water-dispersible powder formulation which is useful for seed treatment and for foliar treatment of plants. While our invention has been described with reference to a number of preferred embodiments, it is to be understood that the scope of our invention is not to be limited to these preferred embodiments. On the contrary, alternatives, changes and/or modifications will readily become apparent to those skilled in the art upon reading our foregoing detailed description. For example, combinations of more than one active ingredient— e.g. fungicide, insecticide, plant growth regulatory agent, and/or biological agent—may be incorporated into the compositions of the present invention. Accordingly, such alternatives, changes and modifications are to be understood as forming a part of our invention insofar as such fall within the spirit and scope of the claims.

We claim:

1. A water-dispersible powder formulation useful for seed treatment and foliar treatment of plants, comprising:

at least one active ingredient, a wetting agent, a dispersant, an anticaking agent, and an adhesion ingredient selected from the group consisting of a sodium salt of a polyacrylic acid, a sodium salt of maleic acid/acrylic acid copolymer, an alkylated polyvinyl pyrrolidone, and mixtures thereof, wherein the wetting agent is present in an amount that is effective for enabling the powder formulation to be wettable by cold water, wherein the dispersant is present in an amount that is effective for enabling the powder formulation to be dispersible in cold water, wherein the anticaking agent is present in an amount that is effective for enabling the formulation to be re-suspendable in water, and wherein the adhesion ingredient is present in an amount that is effective for enabling the formulation to adhere to a plant leaf or seed.

2. The water-dispersible powder formulation of claim 1 further including a plasticizer.

3. The water-dispersible powder formulation of claim 2 wherein the plasticizer is selected from the group consisting of hydrocarbon oil having a boiling point of at least 150° C., vegetable oil, polypropylene glycol, propylene glycol, polyethylene glycol, polyoxypropylene-polyoxyethylene block polymers, polyethylene sorbitan monolaurate and polyether glycol.

4. The water-dispersible powder formulation of claim 1 further including a foam-control agent.

5. The water-dispersible powder formulation of claim 4 wherein the foam-control agent is selected from the group consisting of organic phosphates, silicone fluids with and without silica, sulphonated oils, alcohols, polyols, acetylenic glycol, hydrocarbon oil, fatty acids and esters, and 2-octanol.

6. The water-dispersible powder formulation of claim 1 further including an effervescent.

7. The water-dispersible powder formulation of claim 6 wherein the effervescent comprises an alkaline carbonate and a solid and weak acid.

8. The water-dispersible powder formulation of claim 7 wherein the alkaline carbonate is either an alkali metal, or an alkaline-earth metal, or an ammonium or organoammonium group or cation.

9. The water-dispersible powder formulation of claim 7 wherein the solid and weak acid is either a carboxylic or polycarboxylic acid, or a phosphoric or phosphonic acid, or one of their salts or esters containing an acidic functional group.

10. The water-dispersible powder formulation of claim 1 further including a pigment ingredient.

11. In combination with a water-soluble container, a water-dispersible powder formulation contained within the water-soluble container, wherein the water-dispersible powder formulation is useful for seed treatment and foliar treatment of plants, and wherein the water-dispersible powder formulation comprises:

at least one active ingredient, a wetting agent, a dispersant, an anticaking agent, and an adhesion ingredient selected from the group consisting of a sodium salt of a polyacrylic acid, a sodium salt of maleic acid/acrylic acid copolymer, polyvinyl pyrrolidone, an alkylated polyvinyl pyrrolidone, and mixtures thereof, wherein the wetting agent is present in an amount that is effective for enabling the powder formulation to be wettable by cold water, wherein the dispersant is present in an amount that is effective for enabling the powder formulation to be dispersible in cold water, wherein the anticaking agent is present in an amount that is effective for enabling the formulation to be re-suspendable in water, and wherein the adhesion ingredient is present in an amount that is effective for enabling the formulation to adhere to a plant leaf or seed.

12. The combination of claim 11 wherein the water-dispersible powder formulation further includes a plasticizer.

13. The combination of claim 12 wherein the plasticizer is selected from the group consisting of hydrocarbon oil having a boiling point of at least 150° C., vegetable oil, polypropylene glycol, propylene glycol, polyethylene glycol, polyoxypropylene-polyoxyethylene block polymers, polyethylene sorbitan monolaurate and polyether glycol.

14. The combination of claim 11 wherein the water-dispersible powder formulation further includes a foam-control agent.

15. The combination of claim 14 wherein the foam-control agent is selected from the group consisting of organic phosphates, silicone fluids with and without silica, sulphonated oils, alcohols, polyols, acetylenic glycol, hydrocarbon oil, fatty acids and esters, and 2-octanol.

16. The combination of claim 11 wherein the water-dispersible powder formulation further includes an effervescent.

17. The combination of claim 16 wherein the effervescent comprises an alkaline carbonate and a solid and weak acid.

18. The combination of claim 17 wherein the alkaline carbonate is either an alkali metal, or an alkaline-earth metal, or an ammonium or organoammonium group or cation.

19. The combination of claim 17 wherein the solid and weak acid is either a carboxylic or polycarboxylic acid, or a phosphoric or phosphonic acid, or one of their salts or esters containing an acidic functional group.

20. The combination of claim 11 wherein the water-dispersible powder formulation further includes a pigment ingredient.

* * * * *

UNITED STATES PATENT AND TRADEMARK OFFICE
CERTIFICATE OF CORRECTION

PATENT NO. : 5,719,103

DATED : February 17, 1998

INVENTOR(S) : DAO ET AL.

It is certified that error appears in the above-identified patent and that said Letters Patent is hereby corrected as shown below:

Title page, "Other Publications", line 19, please delete "Defeamers" and insert ---Defoamers--- in its place.

At column 17, line 45, please delete "Scepter" and insert ---Sceptre--- in its place.

At column 17, line 50, please delete "(Scepter durum wheat)" and insert ---(Sceptre durum wheat) in its place.

Signed and Sealed this

Twenty-second Day of September, 1998

Attest:

BRUCE LEHMAN

*Attesting Officer*     *Commissioner of Patents and Trademarks*